(12) United States Patent
Lim et al.

(10) Patent No.: US 11,104,600 B2
(45) Date of Patent: Aug. 31, 2021

(54) DENTAL BULK BLOCK FOR GRINDING PROCESSING AND METHOD OF MANUFACTURING THE SAME

(71) Applicant: HASS CO., LTD., Gangneung-si (KR)

(72) Inventors: Hyung Bong Lim, Ansan-si (KR); Yong Su Kim, Gangneung-si (KR); Kyung Sik Oh, Incheon (KR); Young Pyo Hong, Gangneung-si (KR); Sung Min Kim, Yongin-si (KR); Joon Hyung Kim, Anseong-si (KR); Si Won Son, Seoul (KR); Yena Kim, Seoul (KR)

(73) Assignee: HASS CO., LTD., Gangneung-si (KR)

( * ) Notice: Subject to any disclaimer, the term of this patent is extended or adjusted under 35 U.S.C. 154(b) by 77 days.

(21) Appl. No.: 16/533,128

(22) Filed: Aug. 6, 2019

(65) Prior Publication Data
US 2020/0377403 A1    Dec. 3, 2020

(30) Foreign Application Priority Data

May 29, 2019   (KR) .................. KR10-2019-0063140

(51) Int. Cl.
*C03C 10/00*    (2006.01)
*C03B 27/012*    (2006.01)
(Continued)

(52) U.S. Cl.
CPC ............ *C03B 27/012* (2013.01); *A61K 6/836* (2020.01); *A61K 6/853* (2020.01); *C03B 32/02* (2013.01);
(Continued)

(58) Field of Classification Search
CPC ... C03B 27/012; C03B 32/02; C03C 10/0027; C03C 10/00; C03C 3/085; C03C 3/097; C03C 4/0021; A61K 6/833
See application file for complete search history.

(56) References Cited

U.S. PATENT DOCUMENTS 9,260,342 B2 * 2/2016 Borczuch-Laczka ........................ C03B 32/02
2003/0198838 A1 * 10/2003 Petticrew ............... A61K 6/833
428/701

(Continued)

FOREIGN PATENT DOCUMENTS

KR    10-1975548 B1    5/2019

OTHER PUBLICATIONS

Marcus P. Borom et al, "Strength and Microstructure in Lithium Disilicate Glass-Ceramics", The Pacific Coast Regional Meeting, Oct. 31, 1973, p. 385-391, The American Ceramic Society, San Francisco, CA, Oct. 31, 1973.

*Primary Examiner* — Noah S Wiese
(74) *Attorney, Agent, or Firm* — Novick, Kim & Lee, PLLC; Sang Ho Lee; Hyun Woo Shin

(57) ABSTRACT

Provided is a dental bulk block for grinding processing. The dental bulk block includes a crystalloid, which includes lithium disilicate as a main crystal phase and silicate as a sub-crystal phase, and hyaline as a remainder. The dental bulk block is a functionally gradient material having a crystalline size gradient with respect to a depth thereof and having no interface at a change point of a crystalline size gradient value. The dental bulk block is useful for manufacturing an artificial dental prosthesis that is similar to natural teeth. Accordingly, the time and process for manufacturing the artificial dental prosthesis are shortened, and structural stability is increased in terms of dispersion of (Continued)

force due to gradient functionalization of mechanical properties.

18 Claims, 4 Drawing Sheets

(51) Int. Cl.
- *A61K 6/853* (2020.01)
- *A61K 6/836* (2020.01)
- *C03B 32/02* (2006.01)
- *A61K 6/818* (2020.01)
- *A61K 6/833* (2020.01)
- *C03C 3/085* (2006.01)

(52) U.S. Cl.
CPC .......... *C03C 10/0027* (2013.01); *A61K 6/818* (2020.01); *A61K 6/833* (2020.01); *C03C 3/085* (2013.01)

(56) References Cited

U.S. PATENT DOCUMENTS

| | | | |
|---|---|---|---|
| 2005/0115460 A1* | 6/2005 | Petticrew | B28B 5/04 106/35 |
| 2017/0020639 A1* | 1/2017 | Jahns | A61C 5/77 |

* cited by examiner

DENTAL BULK BLOCK FOR GRINDING PROCESSING AND METHOD OF MANUFACTURING THE SAME

BACKGROUND OF THE INVENTION

1. Field of the Invention

The present invention relates to a dental bulk block for grinding processing, which is useful for manufacturing an artificial-tooth material having structural characteristics similar to those of natural teeth, and a method of manufacturing the same.

2. Description of the Related Art

Crown material is prosthetic material for restoring parts corresponding to dentin and enamel of a damaged tooth, and may be classified into inlays, onlays, veneers, and crowns depending on the application site. Since the position to be restored by the crown material is the outer surface of the teeth, a good aesthetic appearance is critically required, and high strength is required in order to prevent odontoclasis, such as abrasion or chipping, against antagonistic teeth. Examples of conventional materials used as crown materials include leucite crystallized glass (leucite glass-ceramics), reinforced porcelain, or fluorapatite ($Ca_5(PO_4)_3F$) crystallized glass. The materials have excellent aesthetic characteristics but have low strength of 80 to 120 MPa. Accordingly, there is a drawback in that the possibility of odontoclasis is high. Therefore, research currently is underway to develop various high-strength crown materials.

Lithium silicate crystallized glass was introduced by Marcus P. Borom and Anna M. Turkalo in 1973 (The Pacific Coast Regional Meeting, The American Ceramic Society, San Francisco, Calif., Oct. 31, 1973 (Glass division, No. 3-G-73P)).

Crystal phases and strengths have been investigated for various crystal nucleation and growth heat-treatment conditions using $Li_2O$—$Al_2O_3$—$SiO_2$—$Li_2O$—$K_2O$—$B_2O_3$—$P_2O_5$-based glass. Crystal phases of the low-temperature lithium metasilicate and the high-temperature lithium disilicate exhibit strength of 30 to 35 KPS, which is attributable to the residual stress due to the difference in thermal expansion coefficient among the base glass, mother glass, $Li_2SiO_5$, and $Li_2SiO_3$ phases.

Materials and methods for manufacturing artificial teeth using glass containing lithium disilicate crystals (monolithic dental crowns) have already been made known through various patents. However, in the known technologies, it is difficult to perform direct mechanical processing due to the large size of the crystal phase. Accordingly, a lithium metasilicate crystal phase (machinable crystalline) is primarily formed to thus perform processing, and then secondary heat treatment is performed, thus forming a lithium disilicate crystal phase having high strength. Thus, the known technologies have troublesome problems in that a heat treatment process is performed and in that dimensional accuracy is reduced due to shrinkage caused by the heat treatment process. In general, CAD/CAM processing needs to be directly performed in the hospital in order to perform fitting for patients as quickly as possible (one-day appointment). Accordingly, a time delay according to the heat treatment process adds the economic difficulties to patients and users.

Further, a conventional lithium-disilicate-crystallized-glass material has a limitation in realizing high light transmittance and opalescence similar to that of natural teeth due to the coarse crystal phase thereof.

In particular, the conventional lithium-disilicate-crystallized-glass material is used to primarily manufacture lithium metasilicate crystallized glass having good processability for the purpose of processing, and lithium disilicate is formed through secondary crystallization heat treatment after the processing, thus increasing the strength thereof. In this case, the size of the crystal phase is about 3 μm or more. In this state, processability is remarkably decreased, and only the required strength can be realized.

In order to solve these problems, the present applicant proposed a method of manufacturing a crystallized glass containing lithium disilicate and silicate crystal phases having excellent processability by changing a primary heat treatment temperature so as to adjust a crystal size, and received a patent therefor (Korean Patent No. 10-1975548). Specifically, the disclosed method of manufacturing the crystallized glass for teeth containing the silicate crystal phases includes a step of performing primary heat treatment of a glass composition that includes 60 to 83 wt % of $SiO_2$, 10 to 15 wt % of $Li_2O$, 2 to 6 wt % of $P_2O_5$ serving as a nucleation agent, 1 to 5 wt % of $Al_2O_3$, which increases a glass transition temperature and a softening point and which improves the chemical durability of glass, 0.1 to 3 wt % of SrO, which increases the softening point of glass, 0.1 to 2 wt % of ZnO, 1 to 5 wt % of a colorant, and 2.5 to 6 wt % of alkali metal oxide of $Na_2O+K_2O$ for increasing the thermal expansion coefficient of glass at 400 to 850° C.; and a step of performing secondary heat treatment at 780 to 880° C. after the primary heat treatment. The lithium disilicate and silica crystal phases having a nano-size of 5 nm to 2000 nm are generated using the primary heat treatment, and the light transmittance is adjusted using the secondary heat-treatment temperature.

Meanwhile, as the standard of human life has improved, the demand for aesthetics has increased in the field of dentistry. As the desire of patients for good aesthetics has gradually increased, a lot of studies on aesthetic prosthetic restoration using various materials have been conducted.

Examples of factors affecting the aesthetics of porcelain restoration material, as the main aesthetic restoration material that is currently used, include the appearance of the teeth, the surface state, transparency, and color. Among them, transparency is a particularly important factor for successfully manufacturing restoration materials. There has been a lot of research and development on the mechanical and physical properties of porcelain for such aesthetic prosthesis, but there are still a lot of problems regarding matching of colors. Further, there are many difficulties regarding the selection of the color of the restoration material, particularly transparency, in terms of clinical and technical aspects.

In aesthetic prosthodontics, examples of factors affecting aesthetics during tooth restoration include color, the shape and size of the teeth, the arrangement and ratio of teeth, light beams, transmittance, and the design of restorative bodies. In daily life, people are very perceptive to colors and forms. A natural tooth has no parts that have the same color from the neck to the cut surface thereof.

In consideration thereof, recently, a method of manufacturing artificial teeth capable of emulating the deep color of natural teeth using a so-called build-up method has been known.

The build-up method is a method of stacking layers of powder such as porcelain or zirconia, forming a colored artificial tooth, and heat treating the artificial tooth to realize layers having colors similar to those of a natural tooth. Although it is possible to emulate the color of natural teeth very similarly using the build-up method, the aesthetics of artificial teeth are wholly determined by the skill of the technician. Accordingly, the build-up method has problems in that reproducibility is low, the build-up method is not advantageous to the patient because the manufacture thereof using a direct method is impossible, and it is difficult to realize an artificial tooth using a grinding processing method such as CAD/CAM.

Meanwhile, when artificial teeth are manufactured according to a grinding processing method such as CAD/CAM using a conventional bulk block, the bulk block includes materials exhibiting uniform physical properties. Therefore, unlike the natural tooth, it is inevitable to obtain an artificial tooth having a single color. In particular, the artificial tooth according to this method has a problem of deteriorated naturalness because the artificial tooth has an aesthetically foreign appearance when applied to the front tooth.

The transparency and processability are capable of being adjusted through the secondary heat treatment process using the above-described method of manufacturing the crystallized glass described in Korean Patent No. 10-1975548 granted to the present applicant. However, in the case of the crystallized glass thus obtained, a single block has uniform physical properties. Accordingly, in order to realize a deep color as in a natural tooth using the obtained crystallized glass, it is necessary to apply a method of combining a plurality of resultant substances. In other words, it is not easy to directly realize teeth having a natural color by directly subjecting the bulk block to grinding process such as CAD/CAM.

SUMMARY OF THE INVENTION

Accordingly, the present invention has been made keeping in mind the above problems occurring in the related art, and an object of the present invention is to provide a dental bulk block for grinding processing, which is used to manufacture an artificial tooth restoration material exhibiting multi-gradation of transmittance or physical properties similar to those of natural teeth in a manner reproducible through grinding processing such as CAD/CAM without the addition of any other process.

Another object of the present invention is to provide a dental bulk block for grinding processing, which shortens the time and process for manufacturing an artificial dental prosthesis and which has increased structural stability in terms of dispersion of force due to gradient functionalization of mechanical properties.

Yet another object of the present invention is to provide a method of easily manufacturing a dental bulk block for grinding processing, which is used to manufacture an artificial tooth restoration material exhibiting multi-gradation of transmittance or physical properties similar to those of natural teeth.

In order to accomplish the above objects, an embodiment of the present invention provides a dental bulk block for grinding processing. The dental bulk block includes a crystalloid, which includes lithium disilicate as a main crystal phase and silicate as a sub-crystal phase, and hyaline as a remainder. The dental bulk block is a functionally gradient material having a crystalline size gradient with respect to a depth thereof and having no interface at a change point of a crystalline size gradient value.

In the dental bulk block according to the embodiment of the present invention, the crystalline size gradient may be obtained when an average particle diameter is within a range of 5 nm to 5.5 µm.

In the dental bulk block according to the embodiment of the present invention, the crystalline size gradient may be obtained when an average particle diameter is within a range of 5 to 2,000 nm.

In the dental bulk block according to the preferred embodiment of the present invention, the crystalline size gradient may be obtained when an average particle diameter is within a range of 30 to 500 nm.

In the dental bulk block according to the preferred embodiment of the present invention, the crystalline size gradient may be obtained when an average particle diameter is within a range of 300 to 500 nm.

The dental bulk block according to the embodiment of the present invention may have a light transmittance gradient with respect to a depth thereof.

In the dental bulk block according to the preferred embodiment of the present invention, the light transmittance gradient may be within a range of 20 to 80% based on a wavelength of 550 nm.

The dental block according to the embodiment of the present invention may have a flexural strength gradient with respect to a depth thereof.

In the dental block according to the preferred embodiment of the present invention, the flexural strength gradient may be within a range of 250 to 625 MPa.

The dental block according to the embodiment of the present invention may be manufactured using the same glass composition.

In the dental block according to the embodiment of the present invention, the same glass composition may include 60 to 83 wt % of $SiO_2$, 10 to 15 wt % of $Li_2O$, 2 to 6 wt % of $P_2O_5$, 1 to 5 wt % of $Al_2O_3$, 0.1 to 3 wt % of SrO, 0.1 to 2 wt % of ZnO, 1 to 5 wt % of a colorant, and 2.5 to 6 wt % of a mixture of $Na_2O$ and $K_2O$.

Another embodiment of the present invention provides a method of manufacturing a dental bulk block for grinding processing. The method includes manufacturing a block having a predetermined shape using a glass composition including 60 to 83 wt % of $SiO_2$, 10 to 15 wt % of $Li_2O$, 2 to 6 wt % of $P_2O_5$, 1 to 5 wt % of $Al_2O_3$, 0.1 to 3 wt % of SrO, 0.1 to 2 wt % of ZnO, 1 to 5 wt % of a colorant, and 2.5 to 6 wt % of a mixture of $Na_2O$ and $K_2O$, and heat treating the block at a temperature in a range of 400 to 850° C. so as to ensure a temperature gradient in a depth direction of the block.

In the method of manufacturing the dental bulk block according to the embodiment of the present invention, the heat treating may be performed in a gradient-heat-treatment furnace at an operating temperature of 400 to 1,000° C.

A dental bulk block according to the present invention is capable of being readily used to manufacture an artificial tooth restoration material exhibiting multi-gradation of transmittance or physical properties similar to those of natural teeth in a manner reproducible through grinding processing such as CAD/CAM without addition of any other process. It is possible to shorten the time and process for manufacturing an artificial dental prosthesis and to ensure increased structural stability in terms of dispersion of force due to gradient functionalization of mechanical properties. It is possible to manufacture the dental bulk block through a simple process of the gradient heat treatment using a specific glass composition.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
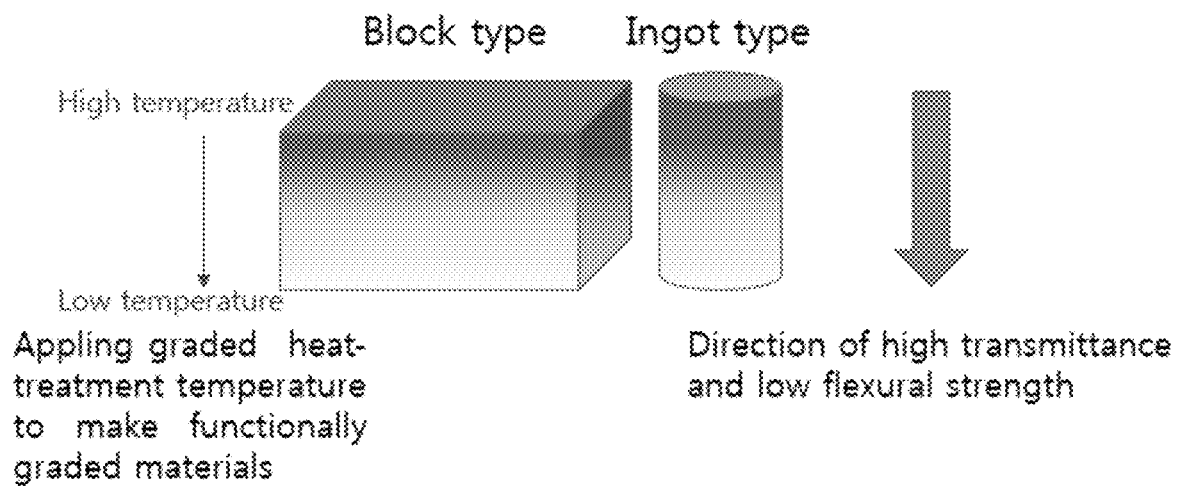
FIG. 1 is a mimetic view showing a method of manufacturing a dental bulk block according to an embodiment of the present invention.

The foregoing and further aspects of the present invention will become more apparent from the following detailed description of preferred embodiments with reference to the accompanying drawings. Hereinafter, these embodiments of the present invention will be described in detail so as to be easily understood and reproduced by those skilled in the art.

A dental bulk block for grinding processing according to the present invention includes a crystalloid, which includes lithium disilicate as a main crystal phase and silicate as a sub-crystal phase, and hyaline as a remainder. The dental bulk block is a functionally gradient material having a crystalline size gradient with respect to a depth thereof and having no interface at a change point of a crystalline size gradient value.

In the above description and the following description, the term 'main crystal phase' may be defined as a crystal phase occupying at least 50 wt % of the entire crystalloid, and the term 'sub-crystal phase' may be defined as a remaining crystal phase other than the main crystal phase in the entire crystalloid.

Further, 'having a crystalline size gradient with respect to a depth' means that there is a gradient of change in the crystalline size when the crystalline size depending on the depth of the bulk block is made in a graph form. That is, the crystalline size is expressed in a gradation form with respect to the depth of the bulk block.

Further, the 'change point of a crystalline size gradient value' means a point at which the gradient value of the change in the crystalline size is substantially changed when the crystalline size depending on the depth of the bulk block is made in a graph form. As used herein, the phrase 'substantially changed' may mean a change in a single numerical value, and may also include a substantial change in the distribution of the value.

Further, the meaning 'having no interface at a change point of a crystalline size gradient value' may be interpreted to mean that there is no significant interface indicating the interlayer separation at the depth point of the bulk block at which the crystalline size gradient value is changed. That is, the bulk block has a crystalline size gradient in a continuous form without any depth-dependent interface.

Meanwhile, the 'functionally gradient material (FGM)' generally refers to a material in which the properties of the constituent material continuously change from one side to the other side. In the present invention, there is substantially no interface and the properties of the constituent material continuously change in the material, and accordingly, the expression of the functionally gradient material is used as a borrowed word.

Such a bulk block includes lithium disilicate as a main crystal phase and silicate as a sub-crystal phase and is capable of being obtained in the form of microcrystals, which may exhibit various sizes and size distributions depending on temperature and may realize various mechanical properties and light transmittances. Further, since the bulk block has a crystalline size gradient with respect to the depth thereof, the bulk block may have gradated light transmittance and mechanical properties with respect to the depth. Moreover, since there is no interface at the change point of the crystalline size gradient value, processing through interlayer bonding is unnecessary, and the problem of layer separation that occurs during grinding processing may be overcome. Further, it is possible to provide an artificial dental prosthesis having increased structural stability in terms of dispersion of force due to gradient functionalization.

In this bulk block of the present invention, the crystalline size gradient may be obtained when an average particle diameter is within the range of 5 nm to 5.5 μm, and preferably within the range of 5 to 2,000 nm.

The bulk block of the present invention is a functionally gradient material. Since the functionally gradient material is applied to grinding processing, for example, CAD/CAM processing, under the same processing conditions, mechinability must be considered. In this respect, the crystalline size gradient may be preferably obtained when the average particle diameter is within the range of 30 to 500 nm.

Further, in view of exhibiting light transmittance that is capable of being clinically used, as in an artificial tooth restoration material, the crystalline size gradient may be preferably obtained when the average particle diameter is within the range of 0.3 to 5.5 μm.

When the aspects of processability and light transmittance are taken into consideration, the crystalline size gradient may be most preferably obtained when the average particle diameter is within the range of 300 to 500 nm.

The dental bulk block of the present invention has the crystalline size gradient described above, and thus it has a light transmittance gradient with respect to the depth thereof.

In particular, in consideration of the range of the average particle diameter with respect to the crystalline size gradient, the light transmittance gradient may be within the range of 20 to 80% based on a wavelength of 550 nm.

Further, the dental bulk block of the present invention has a flexural strength gradient depending on the depth. In particular, in consideration of the range of the average particle diameter with respect to the crystalline size gradient, the flexural strength gradient may be in the range of 250 to 625 MPa.

By manufacturing the dental bulk block of the present invention using the same glass composition, the dental bulk block that includes a crystalloid, including lithium disilicate as a main crystal phase and silicate as a sub-crystal phase, and hyaline as a remainder is obtained. The dental bulk block is a functionally gradient material having a crystalline size gradient with respect to a depth thereof and having no interface at a change point of a crystalline size gradient value. Specifically, the glass composition may include 60 to 83 wt % of $SiO_2$, 10 to 15 wt % of $Li_2O$, 2 to 6 wt % of $P_2O_5$, 1 to 5 wt % of $Al_2O_3$, 0.1 to 3 wt % of SrO, 0.1 to 2 wt % of ZnO, 1 to 5 wt % of a colorant, and 2.5 to 6 wt % of a mixture of $Na_2O$ and $K_2O$.

This glass composition is the composition disclosed in Korean Patent No. 10-1975548, which was filed by the present applicant and for which a patent was granted. The patent discloses that a lithium disilicate crystal phase and a silicate crystal phase are generated through primary heat treatment, the primary heat treatment is particularly performed at 480 to 800° C. in order to increase processing grinding force, and the size of the generated crystal phase is 30 to 500 nm. It also discloses that after the primary heat treatment is performed as described above, crystallized glass that is clinically usable in practice and which has controlled processability and light transmittance is manufactured under a secondary-heat-treatment condition.

The present invention is based on the characteristics exhibited by such a glass composition. The glass is subjected to crystal nucleation and crystal-growth heat treatment for crystallization generation. The temperature at which the crystal nucleus starts to grow from the glass state is 400 to 880° C. In other words, the crystal nucleus starts to form from at least 400° C. and the growth of crystal occurs as the temperature is increased. The growth of crystal exhibits the lowest light transmittance for use as artificial teeth at 850° C. at the maximum. That is, light transmittance is gradually lowered from the temperature at which the crystal starts to grow to a maximum of 850° C. Accordingly, when this crystal growth is realized in a single bulk block, this becomes a technology for emulating the multi-gradation of natural teeth.

All natural teeth have varying light transmittance. If a change in light transmittance depending on the temperature of heat treatment is embodied in a single bulk block, the multi-gradation of natural teeth is capable of being fully realized.

In this respect, the present invention provides a method of manufacturing a dental bulk block for grinding processing. The method includes manufacturing a block having a predetermined shape using a glass composition including 60 to 83 wt % of $SiO_2$, 10 to 15 wt % of $Li_2O$, 2 to 6 wt % of $P_2O_5$, 1 to 5 wt % of $Al_2O_3$, 0.1 to 3 wt % of SrO, 0.1 to 2 wt % of ZnO, 1 to 5 wt % of a colorant, and 2.5 to 6 wt % of a mixture of $Na_2O$ and $K_2O$, and heat treating the block at a temperature in a range of 400 to 850° C. so as to ensure a temperature gradient in a depth direction of the block.

As described above, the composition disclosed in Korean Patent No. 10-1975548, which was filed by the present applicant and for which a patent was granted, exhibits a characteristic in which the light transmittance of the material depends on the range of temperature of heat treatment. When heat treatment is uniformly applied to the whole block, constant light transmittance is exhibited. However, when heat treatment is applied to the block in the presence of a temperature gradient, the multi-gradation of physical properties or light transmittance may be exhibited in a single block.

A bulk-type block is used as a workpiece for CAD/CAM processing. In the manufacturing method of the present invention, when such a block is heat treated, heat is applied to the block with a temperature gradient in a depth direction, thus manufacturing a bulk block having light transmittance and strength with multi-gradation.

Adjusting the light transmittance of conventional crystallized glass is generally difficult due to the large crystal size thereof, and processing thereof is difficult due to the high strength thereof. In contrast, in the case of the glass composition employed in the present invention, microcrystals are capable of being formed, and various sizes and size distributions thereof are exhibited depending on the temperature, and thus the physical properties and light transmittance thereof vary. In view of this, a block may be manufactured using a single glass composition and may then be heat treated with a temperature gradient, thereby embodying multi-gradation of the mechanical properties and light transmittance of a single bulk block.

In this case, 'the step of performing heat treatment with a temperature gradient in the depth direction of the block' means that the temperature is capable of being sequentially increased from the lower end to the upper end in the depth direction of the block and that the temperature gradient is feasible with a partial temperature difference. Of course, the selection of the temperature gradient may depend on the characteristics of the natural teeth of a patient who needs an artificial dental prosthesis or may depend on the unique characteristics of a portion of the tooth requiring the dental prosthesis.

However, in consideration of typical natural teeth, heat treatment may be preferably performed with a temperature gradient in such a manner that the temperature is gradually increased from the lower end to the upper end with respect to the depth of the block.

When the heat treatment method according to the present invention is performed using the above-described glass composition, it is possible to emulate the characteristic in which the light transmittance is low in the gingiva (cervical) side and is increased toward the incisal side in the structure of the natural teeth. This makes the method of the present invention very economically beneficial because there is no need to characterize prostheses separately in the manufacture of prostheses, unlike in the conventional method.

Further, with respect to the physical properties of natural teeth, enamel, which is the surface layer, has high flexural strength but the dentin therein has low strength, thus absorbing and dispersing external forces. In the present invention, it is possible to obtain a functionally gradient material having a mechanical property gradient, particularly a flexural strength gradient, depending on the depth of heat treatment due to the difference in microstructure. Accordingly, physical properties very similar to those of natural teeth are capable of being reproduced.

In an embodiment of the present invention, first, a glass composition that includes 60 to 83 wt % of $SiO_2$, 10 to 15 wt % of $Li_2O$, 2 to 6 wt % of $P_2O_5$ serving as a nucleation agent, 1 to 5 wt % of $Al_2O_3$, which increases a glass transition temperature and a softening point and which improves the chemical durability of glass, 0.1 to 3 wt % of SrO, which increases the softening point of glass, 0.1 to 2 wt % of ZnO, 1 to 5 wt % of a colorant, and 2.5 to 6 wt % of a mixture of $Na_2O$ and $K_2O$ for increasing the thermal expansion coefficient of glass are weighed, followed by mixing. $Li_2CO_3$ may be added instead of $Li_2O$, and carbon dioxide ($CO_2$), which is a carbon (C) component of $Li_2CO_3$, is exhausted in a gas form during the glass melting process. Further, $K_2CO_3$ and $Na_2CO_3$ may be added instead of $K_2O$ and $Na_2O$ in the alkali oxide, respectively, and carbon dioxide ($CO_2$), which is a carbon (C) component of $K_2CO_3$ and $Na_2CO_3$, is exhausted in a gas form during the glass melting process.

The mixing may be performed using a dry mixing process, and a ball-milling process may be used as the dry mixing process. Specifically, in the ball-milling process, a starting raw material is charged into a ball-milling machine, and the ball-milling machine is rotated at a predetermined speed to mechanically pulverize and uniformly mix the starting raw material. The ball used in the ball-milling machine may be a ball including a ceramic material such as zirconia or alumina, and the balls may have the same size or at least two sizes. The size of the ball, the milling time, and the rotation speed per minute of the ball-milling machine are adjusted in consideration of the target particle size. For example, in consideration of the size of the particles, the size of the ball may be set to be in the range of about 1 to 30 mm, and the rotation speed of the ball-milling machine may be set to be in the range of about 50 to 500 rpm. It is preferable to perform the ball milling for 1 to 48 hours in consideration of the target particle size. The starting raw material is pulverized into fine-sized particles, a uniform particle size is ensured, and uniform mixing is performed using the ball milling.

The mixed starting raw material is placed in a melting furnace, and the starting raw material is melted by heating the melting furnace containing the starting raw material. "Melting" means that the starting raw material is changed into a viscous liquid-material state, not a solid state. It is preferable that the melting furnace include a material having a high melting point and a high strength and also having a low contact angle for suppressing the phenomenon in which the molten material is adhered thereto. To this end, preferably, the melting furnace includes a material such as platinum (Pt), DLC (diamond-like carbon), and chamotte, or is coated with a material such as platinum (Pt) or DLC (diamond-like carbon) on the surface thereof.

It is preferable to perform the melting at 1,400 to 2,000° C. under normal pressure for 1 to 12 hours. When a melting temperature is lower than 1,400° C., the starting raw material may not be melted, and when the melting temperature is higher than 2,000° C., excessive energy consumption is required, which is not economical. Therefore, it is preferable to perform the melting at a temperature within the above-described range. Further, when a melting time is very short, the starting raw material may not be sufficiently melted, and when the melting time is very long, excessive energy consumption is required, which is not economical. It is preferable that the temperature increase rate of the melting furnace be about 5 to 50° C./min. When the temperature increase rate of the melting furnace is very slow, a long time is taken, which reduces productivity. When the temperature increase rate of the melting furnace is very fast, since the volatilization amount of the starting raw material is increased due to the rapid temperature increase, the physical properties of the crystallized glass may be poor. Therefore, it is preferable to increase the temperature of the melting furnace at a temperature increase rate within the above-mentioned range. It is preferable that the melting be performed in an oxidation atmosphere such as oxygen ($O_2$) and air.

The molten material is poured into a defined mold in order to obtain the crystallized glass for teeth having the desired shape and size. It is preferable that the mold include a material having a high melting point and a high strength and also having a low contact angle for suppressing the phenomenon in which the glass molten material is adhered thereto. To this end, the mold includes a material such as graphite and carbon. It is preferable that the molten material be preheated to 200 to 300° C. and then be poured into the mold in order to prevent thermal shock.

After the molten material contained in the mold is cooled to 60 to 100° C., the resultant material is transferred to a firing furnace for crystallization heat treatment to thus perform glass nucleation and grow the crystal thereof, thereby manufacturing a crystallized glass.

FIG. 1 is a mimetic view showing a method of performing crystallization heat treatment with a temperature gradient according to the present invention. In the crystallization heat treatment of a block-type or ingot-type bulk block, the heat treatment is performed with a temperature gradient in the depth direction so that the upper end is subjected to heat treatment at high temperatures and the lower end is subjected to heat treatment at low temperatures.

In the above description and the following description, the step of heat treatment with the temperature gradient is not limited to any specific apparatus or method. However, by way of example, the heat treatment may preferably be performed in a gradient-heat-treatment furnace and may be performed at an operating temperature of 400 to 1,000° C. in consideration of the temperature of the heat treatment.

Through the heat treatment with the temperature gradient, in the range from a high-temperature portion to a low-temperature portion thereof, the light transmittance becomes high, there is a light transmittance gradient, the flexural strength becomes low, and there is a flexural strength gradient. This is because the size of the crystal in the crystallized glass is capable of being adjusted depending on the temperature. The crystal phase generated after the heat treatment is performed with a temperature gradient may be lithium disilicate and silicate crystal phases, and may be generated with a temperature gradient of 400 to 850° C. so as to have a crystal-phase-size gradient of 5 to 2,000 nm.

Figure 2:
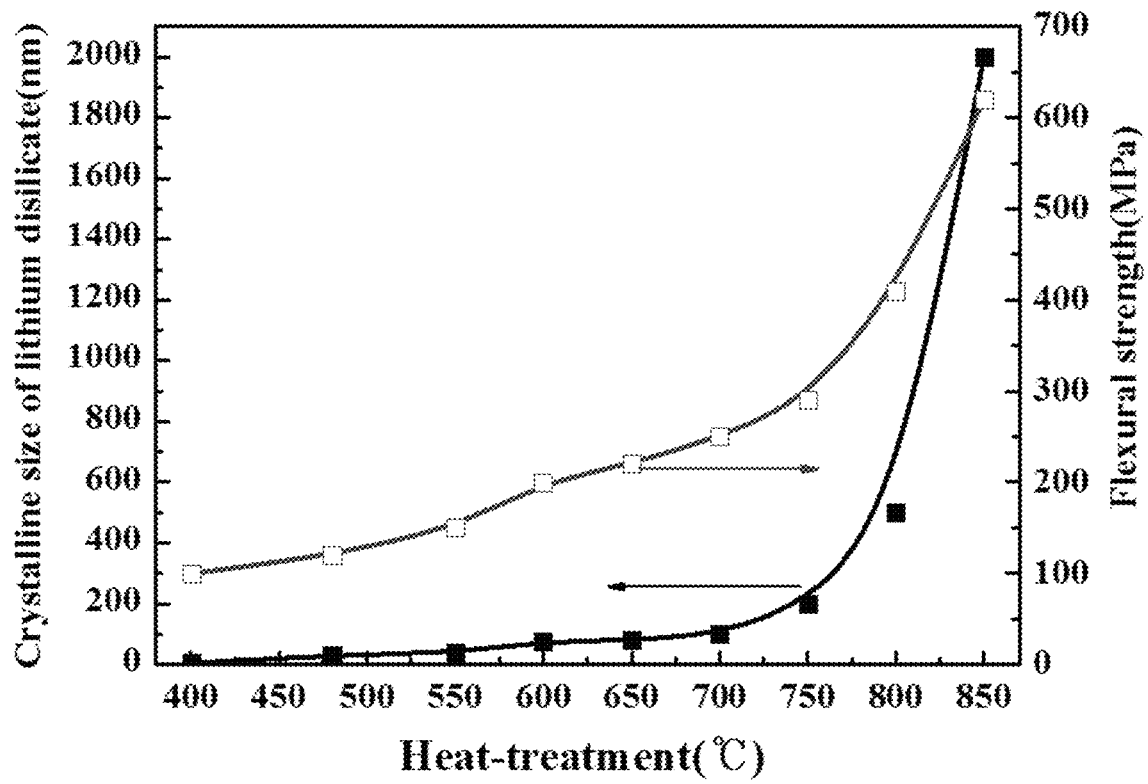
FIG. 2 is a graph showing the results of a change in crystal size (-■-) and a change in flexural strength (-□-) depending on a heat-treatment temperature.

FIG. 2 is a graph showing a change in the average particle diameter of a lithium disilicate crystal phase depending on a heat-treatment temperature (-■-) and a change in the flexural strength of the block depending on the heat-treatment temperature (-□-).

According to FIG. 2, it can be confirmed that when the crystal-phase-size gradient is within the range of 5 to 2,000 nm, the flexural-strength gradient is 250 to 625 MPa.

Meanwhile, in a dental clinic, various light-transmitting products are required, and the light transmittance corresponds to 20 to 55% based on a wavelength of 550 nm. When heat treatment is performed at 780 to 900° C., the transmittance is 55 to 18% (at a wavelength of 550 nm). Since the light transmittance is reduced at temperatures higher than 880° C., the temperature range within which the clinically applicable transmittance is obtained is determined to be 780 to 880° C., and the size of the crystal phase (lithium disilicate or silica) corresponds to 0.3 to 5.0 μm.

Figure 3:
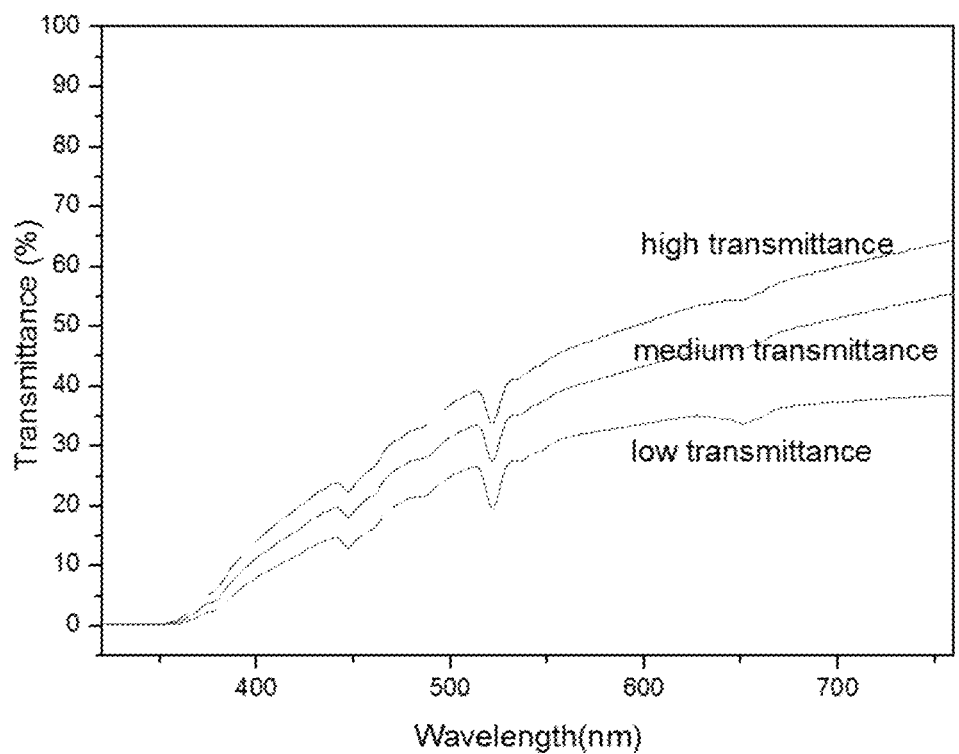
FIG. 3 is a graph showing the result of a light transmission spectrum depending on a heat-treatment temperature, in which the graph marked with low transmittance shows the result of heat treatment at 870° C., the graph marked with medium transmittance shows the result of heat treatment at 825° C., and the graph marked with high transmittance shows the result of heat treatment at 780° C.

FIG. 3 is a graph showing the result of a light transmission spectrum depending on a heat-treatment temperature, in which the graph marked with low transmittance shows the result of heat treatment at 870° C., the graph marked with medium transmittance shows the result of heat treatment at 825° C., and the graph marked with high transmittance shows the result of heat treatment at 780° C.

From the above-described examples, it can be predicted that when a crystallized glass state is obtained through heat treatment from a glass bulk form (block or ingot) using the above-mentioned glass composition, multi-gradation of both light transmittance and physical properties is feasible in a single block by performing heat treatment with a temperature gradient.

The combination of heat treatment with a temperature gradient is achieved by adopting a glass composition having varying properties of size, distribution and density of crystals depending on the temperature of heat treatment, whereby a bulk block, which is a functionally gradient material similar to natural teeth, is obtained. Artificial tooth formation using the bulk block does not require artificial characterization, and makes it easy to realize characteristics similar to those of natural teeth in terms of light transmittance and physical properties.

Figure 4:
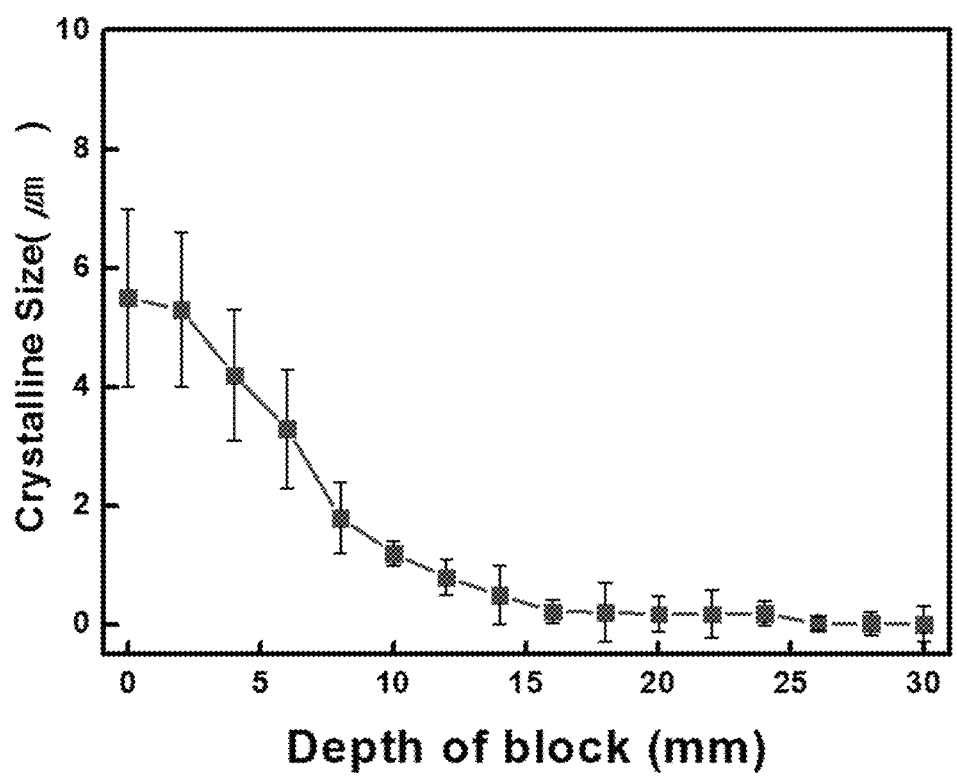
FIG. 4 is a graph showing the particle size of a crystalloid for each depth of the bulk block obtained according to the embodiment of the present invention.

Meanwhile, the particle size of a crystalloid with respect to the depth of the bulk block obtained according to the present invention was analyzed, and is shown in FIG. 4.

Figure 5:
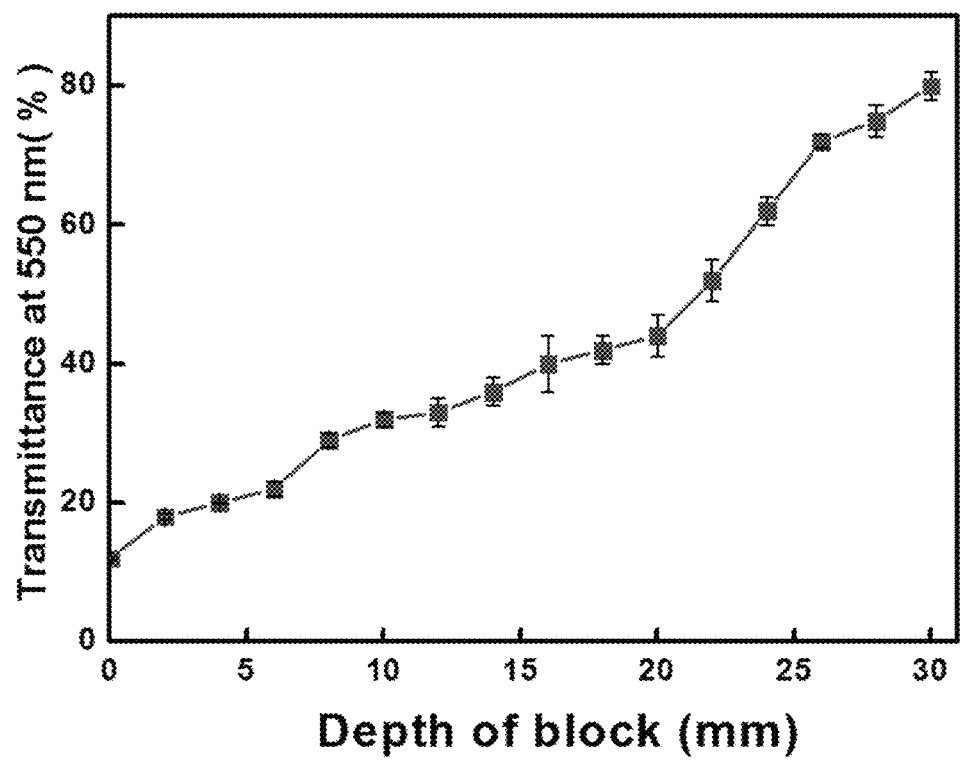
FIG. 5 is a graph showing a change in transmittance for each depth of the bulk block obtained according to the embodiment of the present invention.

Further, a change in the transmittance with respect to the depth of the bulk block obtained according to the present invention was measured, and is shown in FIG. 5.

Figure 6:
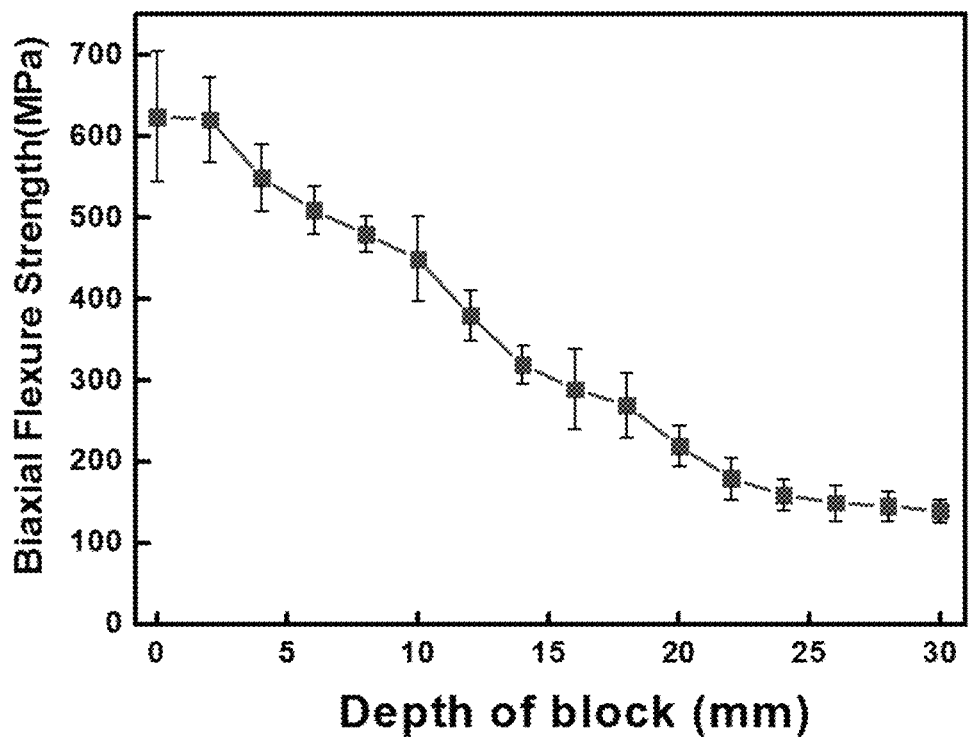
FIG. 6 is a graph showing a change in flexural strength for each depth of the bulk block obtained according to the embodiment of the present invention.
Figure 7:
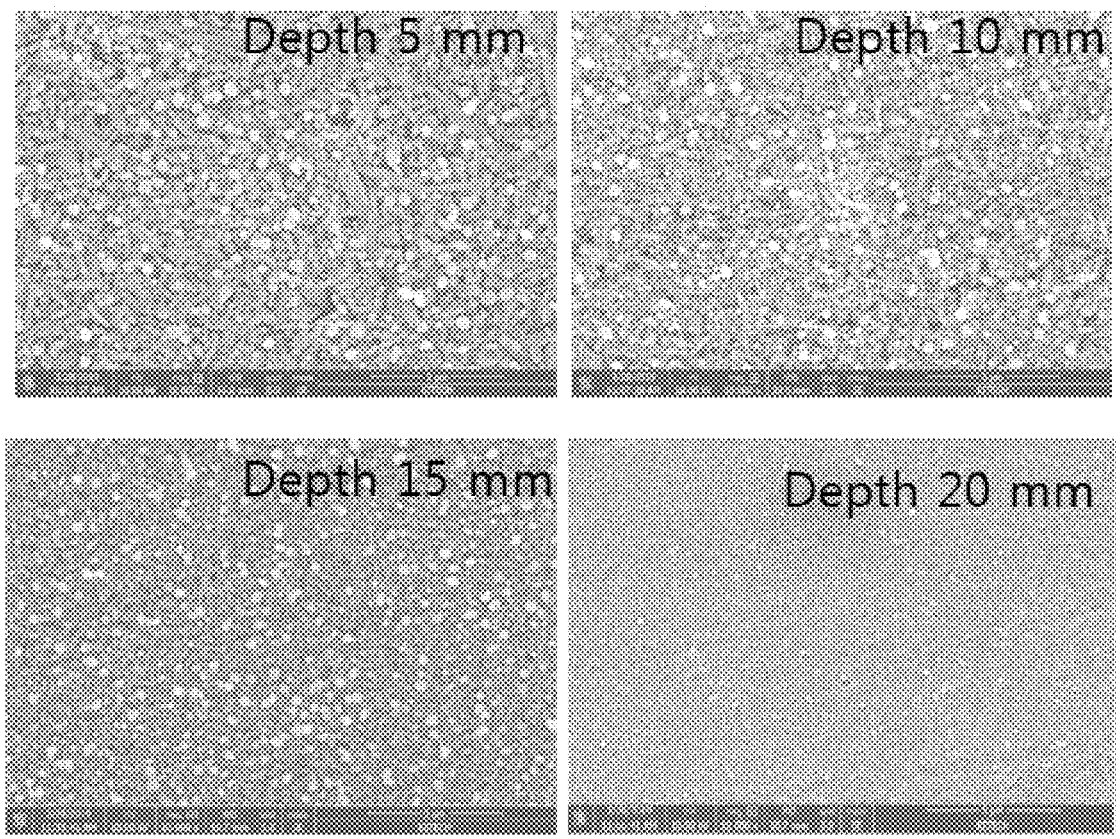
FIG. 7 is a graph showing the microstructure and crystal size for each depth of the bulk block obtained according to the embodiment of the present invention.

Further, a change in flexural strength with respect to the depth of the bulk block obtained according to the present invention was measured, and is shown in FIG. 6.

While the present invention has been particularly described for illustrative purposes with reference to exemplary embodiments thereof shown in the drawings, it will be understood by those of ordinary skill in the art that various modifications and equivalent embodiments are possible within the scope thereof.

What is claimed is:

1. A dental bulk block for grinding processing, comprising:
    a crystalloid, which includes lithium disilicate as a main crystal phase and silicate as a sub-crystal phase, and hyaline as a remainder,
    wherein the dental bulk block is a functionally gradient material having a crystalline size gradient with respect to a depth thereof and having no interface at a change point of a crystalline size gradient value,
    wherein the dental bulk block is manufactured using a same glass composition, and
    wherein the same glass composition includes 60 to 83 wt % of $SiO_2$, 10 to 15 wt % of $Li_2O$, 2 to 6 wt % of $P_2O_5$, 1 to 5 wt % of $Al_2O_3$, 0.1 to 3 wt % of SrO, 0.1 to 2 wt % of ZnO, 1 to 5 wt % of a colorant, and 2.5 to 6 wt % of a mixture of $Na_2O$ and $K_2O$.

2. The dental bulk block of claim 1, wherein the crystalline size gradient is obtained when an average particle diameter is within a range of 5 nm to 5.5 μm.

3. The dental bulk block of claim 1, wherein the crystalline size gradient is obtained when an average particle diameter is within a range of 5 to 2,000 nm.

4. The dental bulk block of claim 1, wherein the crystalline size gradient is obtained when an average particle diameter is within a range of 30 to 500 nm.

5. The dental bulk block of claim 1, wherein the crystalline size gradient is obtained when an average particle diameter is within a range of 300 to 500 nm.

6. The dental bulk block of claim 1, wherein the dental bulk block has a light transmittance gradient with respect to the depth thereof.

7. The dental bulk block of claim 6, wherein the light transmittance gradient is within a range of 20 to 80% based on a wavelength of 550 nm.

8. The dental bulk block of claim 1, wherein the dental bulk block has a flexural strength gradient with respect to the depth thereof.

9. The dental bulk block of claim 8, wherein the flexural strength gradient is within a range of 250 to 625 MPa.

10. A method of manufacturing a dental bulk block for grinding processing, the method comprising:
    manufacturing the block having a predetermined shape using a glass composition including 60 to 83 wt % of $SiO_2$, 10 to 15 wt % of $Li_2O$, 2 to 6 wt % of $P_2O_5$, 1 to 5 wt % of $Al_2O_3$, 0.1 to 3 wt % of SrO, 0.1 to 2 wt % of ZnO, 1 to 5 wt % of a colorant, and 2.5 to 6 wt % of a mixture of $Na_2O$ and $K_2O$; and
    heat treating the block at a temperature in a range of 400 to 850° C. so as to ensure a temperature gradient in a depth direction of the block.

11. The method of claim 10, wherein the heat treating is performed in a gradient-heat-treatment furnace at an operating temperature of 400 to 1,000° C.

12. A dental bulk block for grinding processing, comprising:
    a crystalloid, which includes lithium disilicate as a main crystal phase and silicate as a sub-crystal phase, and hyaline as a remainder,
    wherein the dental bulk block is a functionally gradient material having a crystalline size gradient with respect to a depth thereof and having no interface at a change point of a crystalline size gradient value,
    wherein the dental bulk block has a light transmittance gradient with respect to the depth thereof, and
    wherein the light transmittance gradient is within a range of 20 to 80% based on a wavelength of 550 nm.

13. The dental bulk block of claim 12, wherein the crystalline size gradient is obtained when an average particle diameter is within a range of 5 nm to 5.5 μm.

14. The dental bulk block of claim 12, wherein the crystalline size gradient is obtained when an average particle diameter is within a range of 5 to 2,000 nm.

15. The dental bulk block of claim 12, wherein the crystalline size gradient is obtained when an average particle diameter is within a range of 30 to 500 nm.

16. The dental bulk block of claim 12, wherein the crystalline size gradient is obtained when an average particle diameter is within a range of 300 to 500 nm.

17. The dental bulk block of claim 12, wherein the dental bulk block has a flexural strength gradient with respect to the depth thereof.

18. The dental bulk block of claim 17 wherein the flexural strength gradient is within a range of 250 to 625 MPa.

* * * * *